United States Patent [19]

Campbell et al.

[11] Patent Number: 4,912,202

[45] Date of Patent: Mar. 27, 1990

[54] DIHYDROPYRIDINE RECEPTOR AND ANTIBODIES THERETO

[75] Inventors: Kevin P. Campbell; Toshiaki Imagawa; Albert T. Leung, all of Iowa City, Iowa

[73] Assignee: Miles Inc., Elkhart, Ind.

[21] Appl. No.: 1,788

[22] Filed: Jan. 8, 1987

[51] Int. Cl.[4] .................. C07K 15/00; C07K 3/12; C12N 5/00

[52] U.S. Cl. ................... 530/387; 530/413; 530/809; 435/240.27; 435/70.21; 935/104; 935/108

[58] Field of Search ............... 530/387, 403, 809, 806, 530/413, 841; 435/68, 240.27; 935/104, 108

[56] References Cited

PUBLICATIONS

Schmid, A. et al., "Immunochemical Analysis of Subunit Structures of 1,4-Dihydropyridine Receptors Associated with Voltage-Dependent $Ca^{2+}$ Channels in Skeletal, Cardiac, and Smooth Muscles", *Biochemistry* 25:3492–3495, 1986.

Borsotto, M. et al., "The 1,4–Dihydropyridine Receptor Associated with the Skeletal Muscle Voltage-Dependent $Ca^{2+}$ Channel", *J. Biol. Chem.* 260(26):14255–14263, 1985.

Curtis, B. M. et al., "Purification of the Calcium Antagonist Receptor of the Voltage-Sensitive Calcium Channel from Skeletal Muscle Transverse Tubules", *Biochemistry* 23(10): 2113–2118, May 8, 1984.

Mitchell, R. D. et al., "Purification of Morphologically Intact Tried Structures from Skeletal Muscle", *J. Cell Biol.* 96(4): 1008–16, 1983.

Goding, J. W., *Monoclonal Antibodies:Principles and Practice* Academic Press, Inc., Orlando, 1983, pp. 68–70.

*Primary Examiner*—Margaret Moskowitz
*Assistant Examiner*—Kay E. Cheney
*Attorney, Agent, or Firm*—E. P. Gray; M. G. Boguslaski

[57] ABSTRACT

Monoclonal antibodies capable of immunoprecipitating labeled dihydropyridine receptor material from digitonin-solubilized skeletal muscle triads are disclosed. Said antibodies recognize a 170,000 dalton protein subunit of the dihydropyridine receptor.

4 Claims, No Drawings

DIHYDROPYRIDINE RECEPTOR AND ANTIBODIES THERETO

This work was supported by a grant from the National Institutes of Health (Grant No. HL-37187) and the United States government therefore has rights in the invention.

BACKGROUND OF THE INVENTION

Voltage-dependent $Ca^{2+}$ channels are known to exist in cardiac, skeletal and smooth muscle cells as well as excitable and secretory cells. 1,4-Dihydropyridines are potent blockers of the voltage-dependent $Ca^{2+}$ channel. The 1,4-dihydropyridine receptor has been found to be highly enriched in the transverse tubular membranes of skeletal muscle. Although the dihydropyridine receptor has been purified from transverse tubular membranes of skeletal muscle, its subunit composition remains to be elucidated completely. Curtis et al have shown that it consists of three polypeptides of 160,000 dalton (Da), 50,000 Da and 32,000 Da and that under reducing conditions the apparent molecular weight 160,000 Da subunit shifted to 130,000 Da. Borsotto et al have identified three polypeptides of 142,000 Da, 33,000 Da and 32,000 Da in their preparation of the dihydropyridine receptor. Furthermore, they have shown by immunoblotting with polyclonal antibodies that the 142,000 Da and 32,000 Da subunits are produced by the reduction of a 170,000 Da polypeptide. Recently, Flockerzi et al, using a modification of the procedure of Curtis et al, have shown that the dihydropyridine receptor contains four subunits of 142,000 Da, 122,000 Da, 56,000 Da and 31,000 Da.

The 1,4-dihydropyridine receptor has been purified from rabbit skeletal muscle triads and monoclonal antibodies have been produced that are capable of specifically immunoprecipitating labeled receptor as described hereafter.

SUMMARY OF THE INVENTION

The present invention is directed to a murine monoclonal antibody which is capable of specifically binding a protein subunit of the dihydropyridine receptor of the skeletal muscle calcium channel of skeletal muscle triads, transverse - tubular membranes and purified dihydropyridine receptor separated on SDS - PAGE. Also disclosed is a murine derived hybridoma cell line capable of producing said monoclonal antibody and the use of such antibody in the isolation of the dihydropyridine receptor of voltage - dependent calcium channels.

DETAILED DESCRIPTION OF THE INVENTION

Monoclonal antibodies (MAb) capable of specifically immunoprecipitating the [$^3$H]PN200-110 labeled dihydropyridine receptor (DHPR) of rabbit skeletal muscle have been produced. The designation PN200-110 refers to the compound isopropyl 4-(2,1,3-benzoxadiazol-4-yl)-1,4-dihydro-2,6--dimethyl-pyridine-3,5-dicarboxylic acid 1-methyl ester. BALB/c mice were immunized with skeletal muscle triad vesicles and boosted with DHPR purified from skeletal muscle triads with wheat germ agglutinin (WGA)-Sepharose affinity chromatography and DEA-Ecellulose ion-exchange chromatography. Hybridoma supernatants were initially screened for the production of anti-DHPR antibodies with an immunodot assay. Supernatants that reacted positively against the partially purified DHPR were then screened for their ability to immunoprecipitate the solubilized [$^3$H]PN200-110 labeled dihydropyridine receptor. Monoclonal antibodies from the hybridoma culture supernatants or ascites fluid were preincubated with goat-anti-mouse IgG Sepharose (GAM) beads to form MAb-GAM beads. These monoclonal antibodies beads were then tested for their ability to immunoprecipitate the [$^3$H]PN200-110-labeled dihydropyridine receptor from digitonin solubilized triads. Three monoclonal antibodies were found to immunoprecipitate specifically the [$^3$H]PN200-110-labeled receptor from solubilized triads. All of these antibodies recognized a protein with a relative molecular mass of 170,000 Da on nitrocellulose blots of skeletal muscle triads, transverse-tubular membranes and purified DHPR proteins separated on SDS-PAGE. This 170,000 Da protein was not detected in light sarcoplasmic reticulum membranes or in the void of the WGA-Sepharose column, two preparations that are devoid of DHPR. Wheat-germ agglutinin-peroxidase stained a 175,000 Da protein, demonstrating that the 175,000 Da protein is a glycoprotein component of the purified dihydropyridine receptor. The apparent molecular weight of the 175,000 Da glycoprotein subunit shifts from 175,000 to 150,000 upon reduction. The 170,000 Da polypeptide was not stained by WGA-peroxidase on nitrocellulose blots and its apparent molecular mass did not shift with reduction, indicating that it is different from the 160-kDa glycoprotein of the DHPR described by Curtis et al. The present data demonstrate that the 170,000 Da protein is a subunit of the dihydropyridine receptor of the skeletal muscle $Ca^{2+}$ channel. These results also demonstrate that the 1,4-dihydropyridine receptor of the voltagedependent $Ca^{2+}$ channel from rabbit skeletal muscle contains two dissimilar high molecular weight subunits of 175,000 Da and 170,000 Da.

EXPERIMENTAL PROCEDURES

Preparation of Skeletal Muscle Membranes

Rabbit skeletal muscle triads were isolated according to a modification of the procedure of Mitchell et al in the presence of the following protease inhibitors: aprotinin (76.8 nanomolar, nM), benzamidine (0.83 millimolar, mM), iodoacetamide (1mM), leupeptin (1.1 micromolar, uM), pepstatin A (0.7 uM) and PMSF (0.23 mM), i.e., phenylmethyl sulfonyl fluoride. Briefly, the back and leg muscle were excised from a rabbit, ground and homogenized 3 times for 30 seconds each in 10% sucrose (w:w) in pyrophosphate mix (20 mM sodium pyrophosphate, 20 mM $NaH_2PO_4$ and 1 mM $MgCl_2$, pH 7.1). The homogenate was centrifuged for 15 minutes at 14,300 X g. The supernatant was filtered through cheesecloth and recentrifuged at 30,000 X g for 30 minutes. The pellets were resuspended in 10% sucrose/-pyrophosphate mix and layered onto a gradient of 10%, 14%, 25%, 28%, 36% and 50% sucrose in pyrophosphate mix and centrifuged at 96,500 X g in a Beckman SW 28 rotor for 90 minutes. The fraction at the 28%/35% interface was collected, diluted 4 fold in pyrophosphate mix and then centrifuged for 40 minutes at 158,000 X g. The membrane pellet was resuspended in 10% sucrose/ 20 mM Tris-maleate pH 7.0. The typical yield was 200–300 milligram (mg) of triad vesicles per kilogram (kg) of skeletal muscle and contained 15 25 picomole per milligram (pmoles/mg) of dihydropyridine binding activity.

Light sarcoplasmic reticulum (LSR) vesicles were isolated from adult rabbit skeletal muscle as described by Campbell et al and transverse tubule membrane vesicles were isolated from rabbit skeletal muscle triads according to the French Press procedure of Law et al, both in the presence of protease inhibitors. Protein was determined by the method of Lowry as modified by Peterson [$^3$H]PN200-110 binding was determined as in Glossman et al (1985).

Solubilization of DHPR from Skeletal Muscle Triads

Triad vesicles were labeled with [$^3$H]PN200-110 by incubating with 10–50 nM [$^3$H]PN200-110 (Amersham, specific activity 3.15 TBg/mmole) in Buffer A (i.e., 100 mM NaCl, 50 mM Tris-HCl pH 7.4) at a protein concentration of 2 milligram per milliliter (mg/ml) for 60 minutes at 4° C. and in the presence of 0.1 mM PMSF. The DHPR was solubilized from [$^3$H]PN200-110 labeled triads with 1% digitonin in 0.5M NaCl, 50mM Tris-HCl (pH 7.4) and 0.1 mM PMSF at a protein concentration of 1 mg/ml. After a 30 minute incubation at 4° C. with mild agitation, the mixture was centrifuged at 100,000 X g for 30 minutes and the supernatant containing the solubilized proteins was passed through a 0.2 um membrane filter. The solubilized [$^3$H]PN200-110 receptor was assayed according to the method of Glossman et al (1983).

Purification of Dihydropyridine Receptor

Dihydropyridine receptor was purified by a modification of the procedure of Curtis et al. The triads (100mg) were solubilized with 1% digitonin and applied to 10 ml of WGA-Sepharose 6MB column at a flow rate of 0.2 ml/minute. The column was washed with 10 ml of 50 mM Tris-HCl (pH 7.4), 0.5 M NaCl and 1% digitonin, followed by 500 mM NaCl, 50 mM Tris-HCl (pH 7.4) 0.5 M NaCl and 0.3% digitonin, and again with 50 mM Tris-HCl (pH 7.4) and 0.3% digitonin. The dihydropyridine receptor was then eluted with 20 ml of 200 mM N-acetylglucosamine (NAG) in 50 mM Tris-HCl (pH 7.4) and 0.3% digitonin. Two ml fractions were collected and the fractions enriched in dihydropyridine receptor activity were referred to as the "NAG-eluted dihydropyridine receptor" or "NAG-eluate". The NAG-eluted dihydropyridine receptor was diluted 10 fold in 10 mM Tris-HCl (pH 7.4) and 0.3% digitonin and applied to a DEAE-Cellulose column (2 ml). The column was washed with 10 ml of 50 mM Tris-HCl with 0.3% digitonin and eluted with a 0 to 300 mM NaCl gradient in a total volume of 50 ml. Two ml fractions were collected and the elution of the dihydropyridine receptor was followed by counting the radioactivity of each fraction. The fractions enriched in dihydropyridine receptor were analyzed by SDS-PAGE by the method of Laemmli and Coomassie blue staining.

Immunization and Preparation of Anti-DHPR Monoclonal Antibodies

Female BALB/c mice (5–6 weeks old) were immunized intraperitoneally with 0.5 mg of triad vesicles emulsified in Freund's complete adjuvant. After four weeks, the immunization was repeated three or four times at 2-week intervals with the same amount of triads in Freund's incomplete adjuvant. During the week prior to fusion, two intraperitoneal injections of NAG-eluted dihydropyridine receptor (30 ug) were given followed by an intravenous injection of 40 microgram (ug) of purified dihydropyridine receptor 2 days before fusion. Spleen cells from the mice were fused with NS-1 myeloma cells as described by Kennett. Hybrid cells were grown and passaged in RPMI-1640 medium supplemented with 10% fetal bovine serum. Hybrid cells were subcloned using limiting dilution analysis. Ascites fluid was produced by injecting $5 \times 10^6$ hybridoma cells intraperitoneally into Pristane-primed BALB/c mice. The ascites fluid was de-lipidated with Lipoclean reagent from Cal-biochem.

Immunodot Assay for Anti-DHPR Monoclonal Antibodies

An immunodot assay was used as the initial screening and dilution cloning screening of the hybridoma colonies for antibody production. Light sarcoplasmic reticulum (LSR) vesicles, triads, NAG-eluate and the void from the WGA-Sepharose were dotted (about 0.5 microliter, ul) onto the nitrocellulose at the four quadrants of each well of the Millititer (Millipore) plate and allowed to dry. Specific [$^3$H]PN200-110 binding activity for the preparations dotted were: LSR, 0.5 fmoles/ul; Triads, 21.7 fmoles/ul; WGA-void, 0.1 fmoles/ul; and NAG-eluate, 21.8 fmoles/ul. The plates were blocked with 3% bovine serum albumin-Tris buffered saline (20 mM Tris-HCl, 200mM NaCl, pH 7.5) and incubated with hybridoma supernatants as in the method of Hawkes et al. A goat anti-mouse IgG-peroxidase linked secondary antibody (Copper Laboratories) at 1:1000 dilution in 3% BSA-TBS was used and the plates were developed using 4-chloro-1-naphthol as the substrate. Positive reactions appeared as purple/brown dots. Hybridoma supernatants that reacted with LSR or the void from the WGA-Sepharose column (two preparations that are devoid of DHPR) were eliminated from further testing for anti-DHPR activity. A hybridoma supernatant was considered to be positive in the immunodot assay if it reacted with triads or the NAG-eluted dihydropyridine receptor but showed no reactivity with LSR and the supernatant from the WGA-Sepharose. The serum from the mouse used for the fusion was used as a control in each screening and was shown to be strongly reactive against all the antigens. Wells having positive supernatants were examined for colonies. The colonies were removed from the well and grown up in RPMI 1640 medium supplemented with 10% fetal bovine serum.

Immunoprecipitation Assay from Anti-DHPR Antibodies

Goat-anti-mouse IgG Sepharose beads (Copper) were diluted with Sepharose CL 4B beads to an IgG binding capacity of 1 mg/ml and then washed with 1% BSA in Buffer A, defined supra. Fifteen times bed volume of hybridoma supernatants were incubated with the beads overnight at 4° C. with gentle agitation. The supernatant was then removed and the beads washed once with 200 mM LiCl, 100 mM Tris (pH 7.5) and then twice with Buffer A.

Triad vesicles were labeled with [$^3$H]PN200-110 and solubilized with 1% digitonin as described. The solubilized membranes were then diluted 1:10 with the salt concentration maintained at 50 mM NaCl and 50 mM Tris-HCl (pH 7.4) and 500 ul of this mixture was incubated with 50 ul of GAM-IgG Sepharose at 4° C. for 2 hours with gentle mixing. The mixture was centrifuged in an Eppendorf centrifuge. The supernatants were removed and assayed for DHPR activity using the PEG precipitation assay described by Glossman et al (1985). The beads were washed twice with 1 ml of Buffer A, containing 0.1% digitonin and then counted in 10 ml of scintillation fluid. Each assay was run in triplicate.

The criterion for the specificity of an immunodot assay positive antibody toward the dihydropyridine receptor was its ability to immunoprecipitate the dihydropyridine receptor from solubilized triads. Monoclonal antibodies from hybridoma supernatants were preincubated with goat-anti-mouse IgG beads to form MAb-GAM-IgG beads as described above. These monoclonal antibody beads were then tested for their ability to immunoprecipitate digitonin-solubilized DHPR saturated with [$^3$H]PN200-110. The radioactivity on the beads was counted to determine directly the amount of labeled dihydropyridine receptor precipitated by the antibody. The following controls were performed to establish the validity of this assay: (1) Goatanti-mouse IgG Sepharose by itself or preincubated with the RPMI-1640 medium supplemented with 10% fetal bovine serum, immunoprecipitated a background level of less than 4% of the total [$^3$H]PN200-110 labeled DHPR in the assay mixture; (2) monoclonal antibody beads incubated with [$^3$H]PN200-110 alone in the absence of solubilized triad membranes failed to immunoprecipitate radioactivity beyond the background level; (3) WGA-Sepharose was able to remove 98.1±6.2% of the dihydropyridine receptor from the assay mixture, showing that the solubilized dihydropyridine receptor remained active under the conditions of the assay; and (4) the serum from an immunized mouse used in the fusion was also shown to contain antibodies capable of immunoprecipitating the dihydropyridine receptor. Three antibodies were found to be positive in the immunoprecipitation assay. Antibodies from three hybridomas (prepared as described above) and designated IIF7, IIC12-E1 and IIID5 were able to immunoprecipitate 52.9±1.7, 63.8±8.8 and 48.8±1.6 fmoles of the radiolabeled DHPR from the assay mixture, respectively. The results show that this assay was able to select those anti-dihydropyridine receptor antibodies that do not compete directly with the dihydropyridines for the binding site on the receptor. Hybridomas IIF7, IIC12-E1 and IIID5 are now deposited as part of a permanent culture collection at The University of Iowa. Notably, the antibody produced by hybridoma IIC12-E1 cross-reacts with rabbit cardiac muscle.

Mouse lymphocyte-mouse myeloma hybrid, IIC12-E1, was deposited on Jan. 8, 1987 in the American Type Culture Collection, 12301 Parklawn Drive, Rockville, Md. 20852. Upon issuance of this patent, all restrictions on availability of the deposit to the public wil be lifted.

The amount of [$^3$H]PN200-110 labeled DHPR remaining in the void of the GAM-Beads was determined by the PEG precipitation assay. It was found to correlate inversely with the amount of DHPR immunoprecipitated by the antibody. The anti-dihydropyridine receptor antibodies were shown to bind saturably to the [$^3$H]PN200-110 labeled dihydropyridine receptor. In addition, a close inverse correlation was found between the amount of dihydropyridine receptor immunoprecipitated by the antibody and the amount of [$^3$H]PN200-110 labeled dihydropyridine receptor remaining in the supernatant of the MAb-GAM-Beads as determined by the PEG precipitation assay. In a typical experiment, the highest level of dihydropyridine receptor immunoprecipitated by the monoclonal antibody IIC12 was 29.8±1.9 fmoles (83.9±5.2%) and the amount of dihydropyridine receptor remaining was 5.7±0.5 fmoles (16.1±1.4%). The maximum amount of [$^3$H]PN200-110-labeled dihydropyridine receptor immunoprecipitated by the antidihydropyridine receptor antibodies ranged from 80-95% of the total amount present in the assay mixture, depending upon the preparation of triads and antibody used.

The specificity of the IIID5 antibody with the DHPR was investigated further by carrying out the immunoprecipitation assay in the absence and presence of non-radioactive nitrendipine (a dihydropyridine). Various amounts of IIID5-goat-anti-mouse IgG Sepharose was reacted with [$^3$H]PN200-110 labeled, solubilized DHPR. The amount of specifically and non-specifically labeled DHPR precipitated as a function of IIID5-goat-anti-mouse IgG beads added was determined. The highest level reached corresponded to immunoprecipitation of 193.0±6.2 fmoles (96.3±3.1%) of the total specific [$^3$H]PN200-110 binding activity present in the assay mixture. The immunoprecipitated [$^3$H]PN200-110 was bound to specific dihydropyridine binding sites because immunoprecipitation carried out in the presence of 10 uM nitrendipine precipitated non-specifically bound [$^3$H]PN200-110 representing less than 6% of the total [$^3$H]PN200-110 binding activity in the assay mixture.

Immunoblot Assay

The epitope for each antibody was examined by an indirect immunoperoxidase staining of nitrocellulose blots of skeletal muscle membrane vesicles using a modification of the procedure of Towbin et al. The nitrocellulose blots were blocked with BLOTTO-Bovine Lacto Transfer Technique Optimizer (50 mM NaH$_2$PO$_4$, 0.9% NaCl, pH 7.4, 5% Nonfat Dry Milk) by the method of Johnson et al. The procedure was modified for the staining of the membrane proteins with WGA-peroxidase (Sigma). In this case, the nitrocellulose blots were blocked with 0.5% Tween-PBS (50 mM NaH$_2$PO$_4$, 0.9% NaCl, pH 7.4) and incubated with peroxidase conjugated WGA (1:2000) in 0.5% Tween-PBS. The color was developed as in the immunodot assay using 4-chloronaphthol as the substrate.

The monoclonal antibodies IIC12-E1, IIF7 and IIID5 stained a polypeptide of apparent molecular mass of 170,000 Da on nitrocellulose transfers of transverse tubular membranes, triads and purified DHPR proteins separated on SDS-PAGE. This protein band was not detected in LSR membranes and in the void of the WGA-Sepharose column, two preparations devoid of the DHPR. When the nitrocellulose transfers were stained with peroxidase conjugated WGA, a band of apparent molecular weight of 175,000 Da was stained in transverse tubular membranes, triads and purified DHPR and was absent in LSR and the void of the WGA-Sepharose. This duplicates the observation on Coomassie blue staining of SDS-polyacrylamide gels that the 175,000 and 170,000 Da polypeptides co-purify on WGA-Sepharose chromatography and DEAEcellulose chromatography.

When immunoblots of skeletal muscle triads and purified DHPR under reducing and non-reducing conditions were stained with the monoclonal antibodies IIC12-E1, IIF7 or IIID5, the apparent molecular mass of the 170,000 Da polypeptide remained unchanged. However, when the immunoblots were stained with WGA-peroxidase, the apparent molecular mass of the 175,000 Da polypeptide changed to 150,000 Da upon reduction.

Taken together, these date demonstrate that the monoclonal antibodies of the present invention are capable of immunoprecipitating specific DHPR activity from solubilized skeletal muscle triads. They stain a 170,000 Da polypeptide in skeletal muscle triads and transverse tubular membranes, as well as in DHPR purified from triads by WGA-Sepharose affinity chromatography and DEAE cellulose chromatography. The 170,000 Da polypeptide does not bind to WGA but is co-purified with a 175,000 Da glycoprotein that is a ligand for WGA.

Numerous modifications and variations in the practice of this invention are expected to occur to those skilled in the art upon consideration of the foregoing descriptions of preferred embodiments. Consequently, only such limitations should be placed upon the scope of the invention as appear in the appended claims.

Bibliography

The following publications which have been referred to in the instant specification are expressly incorporated herein by reference:

1. Curtis, B. M., and Catterall, W. A. (1984) Biochemistry 23, 2113–2118.
2. Borsotto, M., Barhanin, J., Fosset, M., and Lazdunski, M. (1985) J. Biol. Chem. 290, 14,255–14,263.
3. Mitchell, R. D., Palade, P., and Fleischer, S. (1983) J. Cell. Biol. 96, 1008–1016.
4. Campbell, K. P., Franzini-Armstrong, C., and Shamoo, A.E. (1980) Biochim. Biophys. Acta. 602, 97–116.
5. Peterson, G. L. (1977) Anal. Biochem. 83, 346–356.
6. Glossman, H., and Ferry, D. (1985) in Methods in Enzymology (Lutz Birbaumer, L., and O'Malley, B. W., eds) Vol. 109, pp. 513–550, Academic Press, New York.
7. Glossman, H., and Ferry, D. R. (1983) Naunyn-Schmiedeberg's Arch. Pharmacol. 323, 279–291.
8. Laemmli, U. K. (1970) Nature 227, 680–685.
9. Kennett, R. H. (1980) In: Monoclonal Antibodies (Kennett, R. H., ed), p. 365, Plenum Press, New York, N.Y.
10. Hawkes, R., Niday, E., and Gordon, J. (1982) Anal. Biochem. 119, 142–147.
11. Johnson, D. A., Gautsch, J. W., Sportsman, J. R., and Elder, J. H. (1984) Gene Anal. Techn. 1, 3–8.
12. Flockerzi, V., Oeken, H.-J., Hoffman, F., Pelzer, D., Cavalie, A., and Trautwein, W. (1986) Nature (London) 323, 66–68.
13. Law, Y. H., Caswell, A. H., and Brunschwig, J.-P. (1977) J. Biol. Chem. 252, 5565–5574.
14. Lowry, O. H., Rosebrough, N. J., Farr, A. L., and Randall, R. J. (1951) J. Biol. Chem. 193, 265–275.

What is claimed is:

1. A murine monoclonal antibody that immunologically binds rabbit cardiac muscle and a protein subunit of the dihydropyridine receptor of the rabbit skeletal muscle calcium channel, said protein subunit having an apparent molecular mass of 170,000 daltons on nitrocellulose blots of rabbit skeletal muscle triads, rabbit transverse tubular membranes and purified rabbit dihydropyridine receptor proteins separated on reducing or non-reducing SDS-PAGE.

2. The murine-derived hybridoma cell line designated IIC12-E1, which produces a monoclonal antibody that immunologically binds rabbit cardiac muscle and a protein subunit of the dihydropyridine receptor of the rabbit skeletal muscle calcium channel, said protein subunit having an apparent molecular mass of 170,000 daltons on nitrocellulose blots of rabbit skeletal muscle triads, rabbit transverse tubular membranes and purified rabbit dihydropyridine receptor proteins separated on reducing or non-reducing SDS-PAGE.

3. The monoclonal antibody produced by the cell line of claim 2.

4. In an immunological procedure for the isolation of the dihydropyridine receptor of the voltage-dependent calcium channel comprising the steps of contacting solubilized rabbit skeletal muscle triads with an antibody that binds a subunit of said receptor for a time and under conditions sufficient for formation of an immune complex between said receptor subunit and said antibody, separating said immune complex from said solubilized rabbit skeletal muscle triads, and isolating said receptor or subunits thereof from said immune complex, the improvement comprising employing as said antibody the monoclonal antibody produced by the hybridoma cell line IIC12-E1.

* * * * *